(12) United States Patent
Clark

(10) Patent No.: US 9,913,440 B2
(45) Date of Patent: Mar. 13, 2018

(54) BARLEY CULTIVAR BG 104

(71) Applicant: Highland Specialty Grains, Inc., Almira, WA (US)

(72) Inventor: Dale R. Clark, Bozeman, MT (US)

(73) Assignee: HIGHLAND SPECIALTY GRAINS, INC., Almira, WA (US)

( * ) Notice: Subject to any disclaimer, the term of this patent is extended or adjusted under 35 U.S.C. 154(b) by 0 days.

(21) Appl. No.: 14/971,818

(22) Filed: Dec. 16, 2015

(65) Prior Publication Data

US 2017/0172092 A1     Jun. 22, 2017

(51) Int. Cl.
*A01H 5/10*     (2006.01)
*A01H 5/00*     (2006.01)
(52) U.S. Cl.
CPC ..................................... *A01H 5/10* (2013.01)
(58) Field of Classification Search
None
See application file for complete search history.

(56) References Cited

U.S. PATENT DOCUMENTS 7,652,202 B2 *   1/2010   Clark ...................... A01H 5/10
                                                                   435/410

OTHER PUBLICATIONS

Barley Growth & Development, 2010, Industry & Investment NSW, ISBN 9781742560250, 1-72.*

* cited by examiner

*Primary Examiner* — Jason Deveau-Rosen
(74) *Attorney, Agent, or Firm* — Lee & Hayes, PLLC

(57) ABSTRACT

A barley cultivar, designated BG 104, is disclosed. The disclosure relates to seeds, plants, and derivatives of barley cultivar BG 104, and methods for producing a barley plant by crossing BG 104 with itself or another barley variety. The disclosure also relates to barley varieties or breeding varieties and plant parts derived from barley BG 104, to methods for producing other barley varieties, lines, or plant parts derived from barley BG 104, and to the barley plants, varieties, and their parts derived from the use of those methods. The disclosure further relates to hybrid barley seeds and plants produced by crossing barley cultivar BG 104 with another barley cultivar. The disclosure relates to methods for developing other barley varieties or breeding lines derived from variety BG 104, including cell and tissue cultures and haploid systems.

24 Claims, No Drawings

… …

BARLEY CULTIVAR BG 104

TECHNICAL FIELD

The present disclosure relates to a new and distinctive barley cultivar designated BG 104.

BACKGROUND

There are numerous steps in the development of a novel, desirable plant germplasm through plant breeding. Plant breeding can begin with the analysis and definition of problems and weaknesses of the current germplasm (e.g., seeds or plant tissue), the establishment of breeding goals, and the establishment of breeding objectives. Then, a germplasm that possess the traits to meet the breeding goals can be selected. The purpose of such plant breeding can be to create an improved combination of desirable traits from multiple parental germplasms in a single variety.

Barley, a type of plant than can be bred, is an important and valuable field crop. Barley breeders seek to develop stable, high yielding barley varieties that are agronomically sound and have good grain quality for its intended use. Barley varieties may differ from each other in one or more traits and can be classified and differentiated according to the specific traits they possess. For example, barley can be two-rowed or six-rowed, which refers to the number and positioning of kernels on the spike (otherwise known as the head). Barley can also be classified as spring barley or winter barley, referring to the growth habit, or by the adherence of hulls on the seed, or by the type of starch in the seed. Additionally, barley varieties can be differentiated based on grain yield, beta-glucan content, lodging, heading date, plant height, awn length, and whether the endosperm is shrunken or plump. Additional traits may also differentiate various barley lines.

SUMMARY OF THE INVENTION

As disclosed herein, there is provided a new barley cultivar designated BG 104. This disclosure relates to the seeds and plants of barley cultivar BG 104, as well as derivatives of the plants of barley cultivar BG 104, and to methods for producing a barley plant produced by crossing the barley cultivar BG 104 with itself or another barley cultivar.

Methods such as selfing, backcrossing, hybrid production, crosses to populations, pedigree breeding, and similar methods using the barley cultivar BG 104 are disclosed herein. Plants produced using barley cultivar BG 104 as at least one parent are also disclosed herein. The barley cultivar BG 104 could be used in crosses with other, different barley plants to produce first generation ($F_1$) barley hybrid seeds and plants with additional or superior characteristics. Also included in the present disclosure are the $F_1$ hybrid barley plants grown from the hybrid seed produced by crossing the barley cultivar BG 104 to a second barley plant. Still further included in the present disclosure are the seeds of a $F_1$ hybrid plant produced with the barley cultivar BG 104 as one parent, the second generation ($F_2$) hybrid barley plant grown from the seed of the $F_1$ hybrid plant, and the seeds of the $F_2$ hybrid plant.

Another aspect of the present disclosure is a method of producing barley seeds comprising crossing a plant of the barley cultivar BG 104 to any second barley plant, including itself or another plant of the cultivar BG 104. In some embodiments, the method of crossing can comprise the steps of: (a) planting seeds of the barley cultivar BG 104; (b) cultivating barley plants resulting from the seeds until the plants bear flowers; (c) allowing fertilization of the flowers of the plants; and (d) harvesting seeds produced from the plants.

Another aspect of the present disclosure is a method of producing hybrid barley seeds comprising crossing the barley cultivar BG 104 to a second, distinct barley plant that is nonisogenic to the barley cultivar BG 104. In some embodiments, the crossing comprises the steps of: (a) planting seeds of barley cultivar BG 104 and a second, distinct barley plant; (b) cultivating the barley plants grown from the seeds until the plants bear flowers; (c) cross-pollinating a flower on one of the two plants with the pollen of the other plant; and (d) harvesting the seeds resulting from the cross pollinating.

Another aspect of the present disclosure is a method for developing a barley plant in a barley breeding program comprising: (a) obtaining a barley plant, or its parts, of the cultivar BG 104; and (b) employing the plant or parts as a source of breeding material using plant breeding techniques. In the method, the plant breeding techniques comprise selfing, backcrossing, hybrid production, crosses to populations, recurrent selection, mass selection, bulk selection, pedigree breeding, or a combination thereof. In some embodiments, the barley plant of cultivar BG 104 may be used as the male or female parent.

Another aspect of the present disclosure is a method of producing a barley plant derived from the barley cultivar BG 104, the method comprising the steps of: (a) preparing a progeny plant derived from barley cultivar BG 104 by crossing a plant of the barley cultivar BG 104 with a second barley plant; and (b) crossing the progeny plant with itself or a second plant to produce a progeny plant of a subsequent generation that is derived from a plant of the barley cultivar BG 104. In one embodiment, the method further comprises: (c) crossing the progeny plant of a subsequent generation with itself or a second plant; and (d) repeating steps (b) and (c) for, in some embodiments, at least 2, 3, 4, or more additional generations to produce an inbred barley plant derived from the barley cultivar BG 104. Also provided by the disclosure is a plant produced by this and the other methods of the disclosure.

In another embodiment, the method of producing a barley plant derived from the barley cultivar BG 104 further comprises: (a) crossing the barley cultivar BG 104-derived barley plant with itself or another barley plant to yield additional barley cultivar BG 104-derived progeny barley seed; (b) growing the progeny barley seed of step (a) under plant growth conditions to yield additional barley cultivar BG 104-derived barley plants; and (c) repeating the crossing and growing steps of (a) and (b) to generate further barley cultivar BG 104-derived barley plants. In some embodiments, steps (a) and (b) may be repeated at least 1, 2, 3, 4, 5, or more times as desired. The disclosure further provides a barley plant produced by this and the foregoing methods.

In another aspect, the present disclosure provides regenerable cells for use in tissue culture of barley plant BG 104. The tissue culture can be capable of regenerating plants having essentially all the physiological and morphological characteristics of the barley plant disclosed herein, and of regenerating plants having substantially the same genotype as the barley plant BG 104. The regenerable cells in such tissue cultures can be the head, awn, leaf, pollen, ovul, embryo, cotyledon, hypocotyl, seed, spike, pericarp, meristematic cell, cell, protoplast, root, root tip, pistil, anther, floret, shoot, stem, callus, or a combination thereof. Still further, the present disclosure can provide barley plants regenerated from the tissue cultures of the barley cultivar BG 104.

In a further aspect, the disclosure provides a composition comprising a seed of barley cultivar BG 104 comprised in plant seed growth media. In certain embodiments, the plant seed growth media is a soil or synthetic cultivation medium. In specific embodiments, the growth medium may be comprised in a container or may, for example, be soil in a field. Plant seed growth media can provide adequate physical support for seeds and can retain moisture and/or nutritional components.

In a further aspect, the disclosure provides a method of producing a commodity plant product comprising collecting the commodity plant product from the plant of barley cultivar BG 104. In some embodiments, the commodity plant product can be, but is not limited to, grain, flour, bran, baked goods, cereals, pasta, beverages, malts, or medicines. The commodity plant product can comprise at least one cell of barley cultivar BG 104.

In yet another aspect, the disclosure provides a barley plant comprising a single locus conversion of the barley cultivar BG 104, wherein the barley plant is otherwise capable of expressing all the physiological and morphological characteristics of the barley cultivar BG 104. In particular embodiments of the subject innovation, the single locus conversion may comprise a transgenic gene that has been introduced by genetic transformation into the barley cultivar BG 104 or a progenitor thereof. In still other embodiments, the single locus conversion may comprise a dominant or recessive allele. The locus conversion may confer potentially any trait upon the single locus converted plant, including, but not limited to, herbicide resistance, insect resistance, resistance to bacterial, fungal, or viral disease, male fertility or sterility, and improved nutritional quality.

In addition to the exemplary aspects and embodiments described above, further aspects and embodiments will become apparent by study of the descriptions that follow.

DEFINITIONS

The following definitions are provided:

Allele. An allele is any of one or more alternative forms of a gene that relate to one trait or characteristic. In a diploid cell or organism, the two alleles of a given gene occupy corresponding loci on a pair of homologous chromosomes.

Awn. Awn means the elongated needle-like appendages on the flower-and-seed-bearing "head" at the top of the barley plant. Awns are attached to lemmas. Lemmas enclose the stamen and the stigma as part of the florets. Florets are grouped in spikelets, which in turn together comprise the head or spike.

Backcrossing. Backcrossing is a process in which a breeder repeatedly crosses hybrid progeny back to one of the parents, for example, a first generation hybrid $F_1$ with one of the parental genotypes of the $F_1$ hybrid.

Barley Yellow Dwarf Virus (BYDV). Barley yellow dwarf virus is a viral disease transmitted by aphids. The symptoms include yellow chlorosis of the older leaves, stunting, sterility, and reduced kernel size.

Beta-Glucan Fiber. Beta-glucan fiber is a nonstarch polysaccharide in which individual glucose molecules (20,000-1,000,000) ae linked by beta 1-4 and beta 1-3 linkages. Beta-Glucan is the main structural material in the cell walls of barley grain.

Beta-Glucan Percentage. Beta-glucan percentage is the percentage of beta-glucan fiber in barley grain.

Cell. Cell includes a plant cell, whether isolated, in tissue culture, or incorporated in a plant or plant part.

Covered Seed. Barley seed can have a cutin layer that cements the hull (lemma and palea or glumes) to the seed. The hull can only be removed by abrasive processing prior to consumption, known as pearling.

Disease Resistance. Disease resistance or disease resistant is defined as the ability of plants to restrict the activities of a specified disease, such as a fungus, virus, or bacterium.

Disease Tolerance. Disease tolerance or disease tolerant is defined as the ability of plants to endure a specified disease (such as a fungus, virus, or bacterium) or an adverse environmental condition and still perform and produce in spite of this condition.

Essentially all of the physiological and morphological characteristics. A plant having essentially all of the physiological and morphological characteristics means a plant having the physiological and morphological characteristics of the recurrent parent, except for the characteristics derived from the converted trait.

Foliar Disease. Foliar disease is a general term for fungal disease that causes yellowing or browning or premature drying of the leaves. The disease typically involves Septoria, net blotch, spot blotch, or scald.

Grain yield. Grain yield, also known as crop yield, is the measure of the yield of a crop per unit area of land cultivated and the seed generation of the plant itself Head. Head refers to a group of spikelets at the top of one plant stem. The term "spike" also refers to the head of a barley plant located at the top of one plant stem.

Herbicide Resistance. Herbicide resistance or herbicide resistant is defined as the ability of plants to survive and reproduce following exposure to a dose of herbicide that would normally be lethal to the plant.

Herbicide Tolerance. Herbicide tolerance or herbicide tolerant is defined as the ability of plants to survive and reproduce after herbicide treatment.

Homozygous Plant. A homozygous plant is defined as a plant with homozygous genes at 95% or more of its loci.

Hulless Seed. Barley seed can have a cutin layer that cements the hull (lemma and palea or glumes) to the seed. The absence of a cutin layer is referred to as hulless. The loose hull can be easily removed at harvest or by minimal cleaning/processing prior to consumption. This has also been referred to as naked or nude seed.

Inbred. Inbred refers to a homozygous plant or a collection of homozygous plants.

Insect Resistance. Insect resistance or insect resistant is defined as the ability of plants to restrict the activities of a specified insect or pest.

Insert Tolerance. Insect tolerance or insect tolerant is defined as the ability of plants to endure a specified insect or pest and still perform and produce in spite of the insect or pest.

Lodging. Lodging refers to the bending or breakage of the plant stem, or the tilting over of the plant, which complicates harvest and can diminish the value of the harvested product.

Leaf Rust. A fungal disease that results in orange-red pustules on the leaf surface. Caused by *Puccinia hordei*.

Net blotch. Net blotch refers to a fungal disease that appears as elongated black lesions running parallel to the leaf veins with distinctive, dark brown net-like patterns. Net blotch is caused by *Pyrenophora teres*.

Percent Identity. Percent identity refers to the comparison of the homozygous alleles of two barley varieties. Percent identity is determined by comparing a statistically significant number of the homozygous alleles of two developed varieties. For example, a percent identity of 90% between barley variety 1 and barley variety 2 means that the two varieties have the same allele at 90% of their loci.

Percent Similarity. Percent similarity refers to the comparison of the homozygous alleles of a barley variety such as BG 104 with another plant, and if the homozygous allele of BG 104 matches at least one of the alleles from the other plant then they are determined to be similar. Percent similarity is determined by comparing a statistically significant number of loci and recording the number of loci with similar alleles as a percentage. A percent similarity of 90% between BG 104 and another plant means that BG 104 matches at least one of the alleles of the other plant at 90% of the loci.

Plant. Plant includes an immature or mature whole plant, including a plant from which seed, grain, or anthers have been removed. A seed or embryo that will produce the plant is also considered to be a plant.

Plant Height (Hgt). Plant height is the average height in inches or centimeters of a group of plants, as measured from the ground level to the tip of the head, excluding awns.

Plant Parts. Plant parts (or reference to "a barley plant, or a part thereof") includes but is not limited to protoplasts, callus, leaves, stems, roots, root tips, anthers, pistils, seeds, grain, pericarps, embryos, pollen, ovules, cotyledons, hypocotyls, spikes, florets, awns, lemmas, shoots, tissues, petioles, cells, meristematic cells, or a combination thereof.

Powdery Mildew. Powdery mildew refers to a fungal disease that results in white to gray powdery pustules on the leaf blade with associated yellowing and browning. Powdery mildew is caused by *Blumeria graminis* f sp. *hordei*.

Progeny. Progeny includes an $F_1$ barley plant produced from the cross of two barley plants where at least one plant includes barley cultivar BG 104. Progeny further includes but is not limited to subsequent $F_2$, $F_3$, $F_4$, $F_5$, $F_6$, $F_7$, $F_8$, $F_9$, and $F_{10}$ generational crosses with the recurrent parental line.

Quantitative Trait Loci (QTL). Quantitative trait loci refer to genetic loci that control to some degree numerically representable traits that are usually continuously distributed.

Scab. Scab refers to a fungal disease that causes salmon-orange spore masses at the base of the glumes and on the seed. It may also cause shriveling of seed. Scab is caused by *Fusarium graminearum*.

Scald. Scald refers to a fungal disease that causes spots to develop on the leaves during cool, wet weather. The spots are oval shaped and the margins of the spots change from bluish-green to zonated brown or tan rings with bleached straw-colored centers. Scald is caused by *Rhynchosporium secalis*.

Septoria. Septoria refers to a fungal disease that appears as elongated, light brown spots on the leaves. It is caused by *Septoria passerinii*.

Single Gene Converted (Conversion). Single gene converted (conversion) plants refers to plants that are developed by a plant breeding technique called backcrossing wherein essentially all of the desired morphological and physiological characteristics of a variety are recovered in addition to the single gene transferred into the variety via the backcrossing technique or via genetic engineering.

Smut, covered. Covered smut refers to a fungal disease in which masses of black spores replace the seed kernels on the head. A persistent membrane can be ruptured during harvest to disperse spores. Covered smut is caused by *Ustilago hordei*.

Smut, loose. Loose smut refers to a fungal disease in which masses of black spores replace the seed kernels on the head. The thin membrane that covers the spores is easily ruptured and spores are disbursed by wind. Loose smut is caused by *Ustilago nuda*.

Spot Blotch. Spot blotch refers to a fungal disease that appears as dark, chocolate-colored blotches forming irregular dead patches on the leaves. Spot blotch is caused by *Cochliobolus sativus*.

Stem rust. Stem rust refers to a fungal disease that produces masses of brick-red pustules on stems and leaf sheaths. Stem rust can be caused by either *Puccinia graminis* f. sp. *tritici* or *Puccinia graminis* f. sp. *secalis*.

Stripe Rust. Stripe rust refers to a fungal disease that results in light yellowish orange pustules arranged in stripes between the veins of the leaves. Stripe rust is caused by *Puccinia striiformis* f. sp. *hordei*.

Waxy Bloom. A waxy or powdery whitish to bluish coating that can be found on the surface of stems, leaves, and spikes. Plant parts that do not have wax are referred to as "glossy." A synonym for presence of the wax is "glaucous."

Waxy Seed. The endosperm of waxy seed contains waxy starch granules with low amylase content. The lower amylase results in seed having an opaque appearance.

Waxy Starch. Starch in grain is stored in granules that can be made of varying amounts of amylopectin (branched) and amylase (straight chained) starch. Waxy starch in barley has low amylase content ranging from 0 to 20%.

DETAILED DESCRIPTION

In the following description, for purposes of explanation, numerous specific details are set forth in order to provide a thorough understanding of the subject innovation. It may be evident, however, that the claimed subject matter may be practiced without these specific details.

One or more examples of the subject innovation are set forth below. Each example is provided by way of explanation of the innovation, not a limitation of the innovation. It will be apparent to those skilled in the art that various modifications and variations may be made to the present innovation without departing from the scope or spirit of the innovation. For instance, features illustrated or described as part of one embodiment can be used on another embodiment to yield a still further embodiment.

Thus, it is intended that the present innovation covers such modifications and variations as come within the scope of the appended claims and their equivalents. Other objects, features, and aspects of the present innovation are disclosed in or are obvious from the following detailed description. It is to be understood by one of ordinary skill in the art that the present discussion is a description of exemplary embodiments only, and is not intended as limiting the broader aspects of the present innovation.

In an embodiment, the innovation is directed to barley cultivar BG 104, its seeds, plants, and hybrids. The presently disclosed cultivar BG 104 can show uniformity and stability for all traits, as described below. The barley BG 104 has been self-pollinated a sufficient number of generations, with attention to uniformity of plant type to ensure homozygosity and phenotypic stability. The cultivar has been increased with continued observation for uniformity in appearance and performance. BG 104 may contain hulled variants at frequencies of up to 18/10,000 seed (0.18%) and or long awned variants at frequencies of up to 18/10,000 plants (0.18%). No other variants are known to occur and BG 104 is a stable and uniform variety in appearance and performance.

BG 104 is a glossy starch, hulless, six-row barley variety created by crossing "BG 006" with "BG 46e." BG 006 is a six-row, covered, waxy starch, spring barley developed from the cross of barley variety Nebula and barley variety Stanuwax. BG 46e is a two-row, hulless, spring barley developed by a male-sterile facilitated recurrent selection population based from the *Prowashonupana* variety. Following the cross of BG 006 and BG 46e described above, $F_1$ seed was planted near Fargo, N. Dak. and $F_2$ seed was harvested therefrom. The $F_2$ seed was planted near Fargo, N. Dak., and spikes were selected from the $F_2$ plants based on seed phenotype and used to plant a bulk $F_3$ population near Yuma, Ariz. Spikes were selected from the $F_3$ plants and planted as a bulk $F_4$ population in Minn., Mont., and N. Dak. Spikes were selected and planted as $F_5$ population near Yuma, Ariz. Desirable plants were selected and seed therefrom was planted as $F_6$ population in 10 foot plots near Bozeman, Mont. Desirable plants were selected and seed therefrom was planted as $F_7$ population in 40 foot strips near Yuma, Ari. $F_8$ population was planted in Bozeman, Mont. and Yuma, Ariz. for testing and for seed increase. $F_9$ population was planted in Bozeman, Mont., again for testing and increase. Uniform appearing strips were harvested, bulked, and designated 'breeder' seed. The seed was designated FA5S09-00104 and was also given the designation F5N09-0104. The variety was given the commercial designation of BG 104.

BG 104 is a six-row, mid-season maturing, semi-dwarf variety adapted to various locations, such as irrigated areas of the Pacific Northwest, including but not limited to Washington, Idaho, and Montana, and moderate adaptation to Arizona and North Dakota, by way of example. BG 104 is most similar in appearance to the variety BG 006. However, BG 104 has short awns while BG 006 has long awns. BG 104 also has a naked or hulless seed, while BG 006 has a covered or hulled seed. Furthermore, BG 104 has seed with a shrunken endosperm, while BG 006 has seed with a plump endosperm. These differences in appearance were observed across the $F_6$ to $F_{10}$ generations. The resultant BG 104 variety also displays higher grain yield than BG 46e, higher grain yield than BG 006 in some instances, lower plant height than both BG 006 and BG 46e, and an average beta-glucan percentage greater than both BG 006 and BG 46e.

Some physical characteristics of BG 104 are listed in Table 1. Comparisons between BG 104 and other barley varieties are presented in Tables 2 through 4. Those skilled in the art will recognize that these are values that may vary due to environment conditions and that other values that are substantially equivalent are within the scope of the present disclosure.

BG 104 can be characterized by a slightly waxy leaf, with no waxy bloom on the spike. BG 104's seeds can be short to mid-long, hulless, and have no hairs on the ventral furrow. The spike of BG 104 can be six-rowed, with an oblong shape and can be covered in hairs on the rachis edge. The glumes of BG 104 can be one-half of the lemma length and can have short, rough hairs completely covering the glumes that are equal to the length of the glume. The lemma can have short awns that are rough with no teeth. BG 104 seeds can have colorless aleurone. The stigma can have many hairs. Additional identifying characteristics of BG 104 are provided below in Table 1.

TABLE 1

| Plant | |
|---|---|
| Growth Habit | Spring |
| Spike | Six-row |
| Juvenile Growth Habit | Semi-prostrate |
| Plant Tillering | Intermediate |
| Maturity (50% flowering) | Mid-season; averages 13 days after planting; 2 days before BG 46e |
| Plant Height | Semi-Dwarf; averages 53 cm; 2 cm shorter than BG 006 |
| Stem Color at Maturity | Yellow |
| Stem Strength | Strong |
| Stem | |
| Exsertion (Flag to Spike at Maturity) | 3-10 cm |
| Anthocyanin | Absent |
| Number of Nodes (Originating from Node Above Ground) | 5 |
| Collar Shape | Open |
| Neck Shape | Straight |
| Leaves | |
| Coleoptile Color | Green |
| Basal Leaf Sheath Pubescence at Seedling Stage | Absent |
| Basal Leaf Sheath Color | Green |
| Leaf Color at Boot | Green |
| Flag Leaf at Boot | Upright |
| Pubescence on Leaf (first leaf below flag leaf) Blade | Absent |
| Pubescence on Leaf (first leaf below flag leaf) Sheath | Absent |
| Auricle Color: | White |
| Pubescence on Auricle: | Absent |
| Basal Leaf Sheath (Seedling) | Glabrous |
| Waxiness | Slightly Waxy |
| Width (First Leaf Below Flag Leaf) | 11.76 mm |
| Length (First Leaf Below Flag Leaf) | 19.43 cm |
| Anthocyanin in Leaf Sheath | Absent |
| Spike | |
| Exsertion | Slight |
| Shape | Oblong |
| Density | Erect (Dense) |
| Position at Maturity | Inclined |
| Waxy Bloom | Absent (Glossy) |
| Lateral Kernels Overlap | At tip |
| Hairiness of Rachis Edge | Covered |
| Lemma | |
| Awns | Short (less than equal to length of spike) |
| Awn Surface | Rough |
| Teeth | Absent |
| Hair | Absent |
| Shape of Base | Depression |
| Rachilla Hairs | Long |
| Glumes | |
| Length | One-half of Lemma |
| Hairiness | Completely Covered |
| Length of Hairs | Short |
| Glume Awn Surface | Rough |
| Glume Awn Length Relative to Glume Length | Shorter that Glume |
| Stigma | |
| Hairs | Many |
| Seed | |
| Hull Type (Lemma/Palea Adherence) | Hulless (naked) |
| Hairs on Ventral Furrow | Absent |
| Shape of Base | Slight crease |
| Kernel Aleurone Color | Colorless |

TABLE 1-continued

| | |
|---|---|
| Kernel Length | Short to Mid-Long (7.5-9.0 mm) |
| Wrinkling of Hull | Naked |
| Average 1,000 Kernel Weight | 26 g |
| Diseases | |
| Powdery Mildew | Intermediate |

The barley cultivar BG 104, as described above, has been tested for tolerance to diseases that are known to affect plants. Specifically, the barley cultivar BG 104 was tested to determine its tolerance against powdery mildew, for example. The barley cultivar BG 104 can have intermediate tolerance to powdery mildew. Additional tolerances are achievable through genetic modification methods described below.

This disclosure is also directed to a composition comprising a seed of BG 104 comprised in plant seed growth media. Plant seed growth media can provide adequate physical support for seeds and can retain moisture and/or nutritional components. In embodiments, the plant seed growth media can be a soil or synthetic cultivation medium. In some embodiments, the growth medium may be comprised in a container or may, for example, be soil in a field.

This disclosure is also directed to methods for producing a barley variety by crossing a first parent barley variety with a second parent barley variety, wherein the first or second barley variety is the variety BG 104. Therefore, any methods using the barley variety BG 104 are part of this disclosure, including selfing, backcrossing, hybrid production, crosses to populations, recurrent selection, mass selection, bulk selection, pedigree breeding, mutagenesis, and transgenic modification. Any plants produced using barley variety BG 104 as a parent are within the scope of this disclosure.

Further reproduction of the barley variety BG 104 can occur by tissue culture and regeneration to produce barley plants capable of having the physiological and morphological characteristics of barley variety BG 104.

A further embodiment of the present disclosure is a backcross conversion of barley variety BG 104. A backcross conversion occurs when DNA sequences are introduced through non-transformation breeding techniques, such as backcrossing. Desired traits transferred through this process include, but are not limited to, higher grain yield, shorter plant height, and increased beta-glucan percentage. The trait of interest can be transferred from the donor parent to the recurrent parent, in this case, the barley plant disclosed herein. Single gene traits may result from either the transfer of a dominant allele or a recessive allele. Selection of progeny containing the trait of interest can be done by direct selection for a trait associated with a dominant allele. Selection of progeny for a trait that is transferred via a recessive allele may require growing and selfing the first backcross to determine which plants carry the recessive alleles. Recessive traits may require additional progeny testing in successive backcross generations to determine the presence of the gene of interest.

Another embodiment of this disclosure is a method of developing a backcross conversion BG 104 barley plant that can involve the repeated backcrossing to barley variety BG 104. The number of backcrosses made may be 2, 3, 4, 5, 6, or greater, and the specific number of backcrosses used will depend upon the genetics of the donor parent and whether molecular markers are utilized in the backcrossing program. Using backcrossing methods, one of ordinary skill in the art can develop individual plants and populations of plants that retain at least 70%, 75%, 79%, 80%, 81%, 82%, 83%, 84%, 85%, 86%, 87%, 88%, 89%, 90%, 91%, 92%, 93%, 94%, 95%, 96%, 97%, 98%, or 99% of the genetic profile of barley variety BG 104. The percentage of the genetics retained in the backcross conversion may be measured by either pedigree analysis or through the use of genetic techniques such as molecular markers or electrophoresis.

In pedigree analysis, on average 50% of the starting germplasm could be passed to the progeny line after one cross to another line, 75% after backcrossing once, 87.5% after backcrossing twice, and so on. Molecular markers could also be used to confirm and/or determine the recurrent parent used. The backcross conversion developed from this method may be similar to BG 104 for the results listed in Table 1. Such similarity may be measured by a side by side phenotypic comparison. Any such comparison should be made in environmental conditions that account for the trait being transferred.

Another embodiment of the disclosure is an essentially derived variety of BG 104. Essentially derived varieties may be obtained for example by the selection of a natural or induced mutant, or of a somaclonal variant, the selection of a variant individual from plants of the initial variety, or backcrossing. An essentially derived variety of BG 104 may further be considered as one whose production requires the repeated use of variety BG 104 or is predominately derived from variety BG 104.

This disclosure is also directed to methods for using barley variety BG 104 in plant breeding. One such embodiment is the method of crossing barley variety BG 104 with another variety of barley to form a first generation population of $F_1$ plants. This disclosure also includes the population of first generation $F_1$ plants produced by this method. This first generation population of $F_1$ plants may comprise a substantially complete set of the alleles of barley variety BG 104. One of ordinary skill in the art may utilize either breeder books or molecular methods to identify a particular $F_1$ plant produced using barley variety BG 104. These embodiments also include use of backcross conversions of barley variety BG 104 to produce first generation $F_1$ plants.

A method of developing BG 104-progeny barley plants comprising crossing BG 104 with a second barley plant and performing a breeding method is also disclosed herein. One of ordinary skill in the art may cross barley variety BG 104 with another variety of barley. The $F_1$ seed derived from this cross may be grown to form a homogeneous population. The $F_1$ seed may contain one set of the alleles from variety BG 104 and one set of the alleles from the other barley variety. The $F_1$ genome may be made up of 50% variety BG 104 and 50% of the other variety. The $F_1$ seed may be grown and allowed to self, thereby forming $F_2$ seed. On average, the $F_2$ seed may have derived 50% of its alleles from variety BG 104 and 50% from the other barley variety, but various individual plants from the population may have a greater percentage of their alleles derived from BG 104. The $F_2$ seed may be grown and selection of plants may be made based on visual observation and/or measurement of traits. The BG 104-derived progeny that exhibit one or more of the desired BG 104-derived traits may be selected and each plant may be harvested separately. This $F_3$ seed from each plant may be grown in individual rows and allowed to self. Then selected rows or plants from the rows may be harvested and threshed individually. The selections may again be based on visual observation and/or measurements for desirable traits of the plants, such as one or more of the desirable BG 104-derived traits. The process of growing and selection may be repeated any number of times until a homozygous BG 104-derived barley plant is obtained. The homozygous BG 104-derived barley plant may contain desirable traits derived from barley variety BG 104, some of which may not have been expressed by the other original barley variety to which barley variety BG 104 was crossed and some of which may have been expressed by both barley varieties but now would be at a level equal to or greater than the level expressed in barley variety BG 104. The homozygous BG 104-derived barley plants may have, on average, 50% of their genes derived from barley variety BG 104, but various individual plants from the population may have a greater percentage of their alleles derived from BG 104. The breeding process of crossing, selfing, and selection may be repeated to produce another population of BG 104-derived barley plants with, on average, 25% of their genes derived from barley variety BG 104, but various individual plants from the population may have a greater percentage of their alleles derived from BG 104. Another embodiment of the disclosure is homozygous BG 104-derived barley plants that have received BG 104-derived traits.

The previous example can be modified in numerous ways. For instance, selection may occur at every selfing generation; selection may occur before or after the actual self-pollination process occurs; or individual selections may be made by harvesting individual spikes, plants, rows, or plots at any point during the breeding process described herein. In addition, double haploid breeding methods may be used at any step in the process. The population of plants produced at each and any generation of selfing is also described herein, and each such population may consist of plants containing approximately 50% of its genes from barley variety BG 104, 25% of its genes from barley variety BG 104 in the second cycle of crossing, selfing, and selection, 12.5% of its genes from barley variety BG 104 in the third cycle of crossing, selfing, and selection, and so on.

Another embodiment of this disclosure is the method of obtaining a homozygous BG 104-derived barley plant by crossing barley variety BG 104 with another variety of barley and applying double haploid methods to the $F_1$ seed or $F_1$ plant or to any generation of BG 104-derived barley obtained by the selfing of this cross.

Still further, this disclosure is directed to methods for producing BG 104-derived barley plants by crossing barley variety BG 104 with a barley plant and growing the progeny seed, and repeating the crossing or selfing along with the growing steps with the BG 104-derived barley plant from 1 to 2 times, 1 to 3 times, 1 to 4 times, or 1 to 5 times. Thus, any and all methods using barley variety BG 104 in breeding are part of this disclosure, including selfing, backcrossing, hybrid production, crosses to populations, recurrent selection, mass selection, bulk selection, and pedigree breeding. Unique starch profiles, molecular marker profiles, and/or breeding records can be used by those of ordinary skill in the art to identify the progeny lines or populations derived from these breeding methods.

Still further, this disclosure is directed to methods for producing BG 104-derived barley plants by pedigree breeding. Pedigree breeding starts with the crossing of two genotypes, such as BG 104 and another barley variety having one or more desirable characteristics that is lacking or that complements BG 104. If the two original parents do not provide all the desired characteristics, other sources can be included in the breeding population. In the pedigree breeding method, plants exhibiting desired traits are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations can serve to increase seed of the developed variety. In an embodiment, the developed variety comprises homozygous alleles at about 95% or more of its loci.

In addition, this disclosure encompasses progeny with the same or greater grain yield of BG 104, the same or shorter plant height, and the same or more beta-glucan percentage of BG 104. The expression of these traits may be measured by agronomic performance testing. Any such comparison should be made in the same environmental conditions.

This disclosure is also directed to a transgenic variant of BG 104. A transgenic variant of BG 104 may contain at least one transgene but could contain at least 1, 2, 3, 4, 5, 6, 7, 8, 9, 10, or more transgenes. In another embodiment, a transgenic variant of BG 104 may contain no more than 15, 14, 13, 12, 11, 10, 9, 8, 7, 6, 5, 4, 3, or 2 transgenes. Another embodiment of the disclosure involves a process for producing barley cultivar BG 104 further comprising a desired trait. The process can comprise introducing a transgene that confers a desired trait to a barley plant of cultivar BG 104. As part of the disclosure, one of ordinary skill in the art may utilize any method of producing transgenic plants that is currently known or yet to be developed.

In another embodiment, the method may involve the creation of variants by mutagenesis or transformation of barley cultivar BG 104. All plants produced using barley cultivar BG 104 as at least one parent are considered within the scope of this disclosure.

The present disclosure also provides for single or multiple gene converted plants of barley cultivar BG 104. The transferred gene(s) may be a dominant or recessive allele. The transferred gene(s) may confer such traits as herbicide tolerance or resistance, insect tolerance or resistance, tolerance or resistance to bacterial, fungal, or viral disease, male fertility, male sterility, enhanced nutritional quality, modified fatty acid metabolism, modified carbohydrate metabolism, modified seed yield, modified protein percent, modified beta-glucan percent, modified lodging resistance, modified lipoxygenase, beta-glucanase and/or polyphenol oxidase content and/or activity, and/or industrial usage, or a combination thereof. The gene may be a naturally occurring barley gene or a transgene introduced through genetic engineering techniques.

Any method for plant transformation known in the art may be utilized in the present innovation. The disclosure comprises transgenic methods including, but not limited to, expression vectors introduced into plant tissues using a direct gene transfer method such as microprojectile-mediated delivery, DNA injection, electroporation and the like. In an embodiment, expression vectors may be introduced into plant tissues by using either microproj ectile-mediated delivery with a biolistic device or by using *Agrobacterium*-mediated transformation. Transformed plants obtained with the protoplasm of barley cultivar BG 104 are intended to be within the scope of this disclosure.

Various genetic elements can be introduced into the plant genome using transformation. These elements include but are not limited to genes, coding sequences, inducible, constitutive, and tissue-specific promoters, enhancing sequences and signal, and targeting sequences.

In embodiments, a genetic trait that has been engineered into a barley BG 104 plant using transformation techniques could then be moved into another line using traditional breeding techniques that are known in the plant breeding arts. For example, a backcrossing approach could be used to move a transgene from a transformed barley BG 104 plant to another barley variety and the resulting progeny would comprise a transgene.

Likewise, in an embodiment, agronomic genes can be expressed in transformed BG 104 plants. More particularly, plants can be genetically engineered to express various phenotypes of agronomic interest. Through the transformation of BG 104 plants, the expression of genes can be modulated to enhance disease tolerance or resistance, insect tolerance or resistance, herbicide tolerance or resistance, water stress tolerance, agronomic traits, and/or grain quality traits, for example. Transformation can also be used to insert DNA sequences that control or help control male sterility. DNA sequences native to barley as well as nonnative DNA sequences can be transformed into barley and used to modulate levels of native or nonnative proteins. Antisense technology, various promoters, targeting sequences, enhancing sequences, and other DNA sequences can be inserted into the BG 104 barley genome for the purpose of modulating the expression of proteins. Exemplary genes that can be inserted into the BG 104 barley genome as part of the present disclosure include, but are not limited to, those categorized below.

Genes that Confer Tolerance or Resistance to Pests or Disease (A) Plant disease resistance genes. Plant defenses are often activated by specific interaction between the product of a disease resistance gene (R) in the plant and the product of a corresponding avirulence (Avr) gene in the pathogen. In embodiments, a BG 104 plant variety can be transformed with a cloned resistance gene to engineer plants that are tolerant or resistant to specific pathogen strains.

*Fusarium* head blight along with deoxynivalenol both produced by the pathogen *Fusarium graminearum* Schwabe have caused devastating losses in barley production. Genes expressing proteins with antifungal action can be used as transgenes to prevent *Fusarium* head blight. Various classes of proteins have been identified. Examples include endochitinases, exochitinases, glucanases, thionins, thaumatin-like proteins, osmotins, ribosome inactivating proteins, flavonoids, and lactoferricin. During infection with *Fusarium graminearum*, deoxynivalenol is produced. There is evidence that production of deoxynivalenol increases the virulence of the disease. Genes with properties for detoxification of deoxynivalenol have been engineered for use in barley. A synthetic peptide that competes with deoxynivalenol has also been identified. Changing the ribosomes of the host so that they have reduced affinity for deoxynivalenol has also been used to reduce the virulence of *Fusarium graminearum*.

Genes used to help reduce *Fusarium* head blight include, but are not limited to, Tri101 (*Fusarium*), PDR5 (yeast), tlp-1 (oat), tlp-2 (oat), leaf tlp-1 (wheat), tip (rice), tlp-4 (oat), endochitinase, exochitinase, glucanase (*Fusarium*), permatin (oat), seed hordothionin (barley), alpha-thionin (wheat), acid glucanase (alfalfa), chitinase (barley and rice), class beta II-1,3-glucanase (barley), PR5tlp (*Arabidopsis*), zeamatin (maize), type 1 RIP (barley), NPR1 (*Arabidopsis*), lactoferrin (mammal), oxalyl-CoA-decarboxylase (bacterium), IAP (baculovirus), ced-9 (*C. elegans*), and glucanase (rice and barley).

(B) A gene conferring tolerance or resistance to a pest.

(C) A gene conferring resistance to such diseases as barley rusts, *Septoria tritici, Septoria nodorum*, powdery mildew, *Helminthosporium* diseases, smuts, bunts, *Fusarium* diseases, bacterial diseases, and viral diseases.

(D) A *Bacillus thuringiensis* protein, a derivative thereof, or a synthetic polypeptide modeled thereon.

(E) An insect-specific hormone or pheromone such as an ecdysteroid or juvenile hormone, a variant thereof, a mimetic based thereon, or an antagonist or agonist thereof (F) An insect-specific peptide that, upon expression, disrupts the physiology of the affected pest.

(G) An enzyme responsible for hyperaccumulation of a monoterpene, a sesquiterpene, a steroid, hydroxamic acid, a phenylpropanoid derivative, or another non-protein molecule with insecticidal activity.

(H) An enzyme involved in the modification, including the post-translational modification, of a biologically active molecule. For example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and/or a glucanase, whether natural or synthetic.

(I) A molecule that stimulates signal transduction.

(J) A hydrophobic moment peptide.

(K) A membrane permease, a channel former, or a channel blocker.

(L) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses.

(M) An insect-specific antibody or an immunotoxin derived therefrom. Thus, an antibody targeted to a critical metabolic function in the insect gut would inactivate an affected enzyme, killing the insect.

(N) A virus-specific antibody.

(O) A developmental-arrestive protein produced in nature by a pathogen or a parasite. For example, fungal endo-alpha-1,4-D-polygalacturonases facilitate fungal colonization and plant nutrient release by solubilizing plant cell wall homoalpha-1,4-D-galacturonase.

(P) A developmental-arrestive protein produced in nature by a plant.

(Q) Genes involved in the Systemic Acquired Resistance response and/or pathogenesis-related genes.

(R) Antifungal genes.

(S) Detoxification genes, such as for fumonisin, beauvericin, moniliformin, zearalenone, and their structurally related derivatives.

(T) Cystatin and cysteine proteinase inhibitors.

(U) Defensin genes.

(V) Genes conferring resistance to nematodes.

Genes that Confer Tolerance or Resistance to an Herbicide (A) Acetohydroxy acid synthase. Acetohydroxy acid synthase, which has been found to make plants that express this enzyme resistant to multiple types of herbicides, has been introduced into a variety of plants. Other genes that confer tolerance to herbicides include: a gene encoding a chimeric protein of rat cytochrome P4507A1 and yeast NADPH-cytochrome P450 oxidoreductase, genes for glutathione reductase and superoxide dismutase, and genes for various phosphotransferases.

(B) An herbicide that inhibits the growing point or meristem, such as an imidazolinone or a sulfonylurea.

(C) Glyphosate (resistance imparted by mutant 5-enolpyruvl-3-phosphoshikimate synthase (EPSP) and aroA genes, respectively) and other phosphono compounds such as glufosinate (phosphinothricin acetyl transferase (PAT) and *Streptomyces hygroscopicus* PAT (bar) genes), and pyridinoxy or phenoxy proprionic acids and cyclohexones (ACCase inhibitor-encoding genes). Glyphosate resistance is also imparted to plants that express a gene that encodes a glyphosate oxido-reductase enzyme. In addition, glyphosate resistance can be imparted to plants by the over-expression of genes encoding glyphosate N-acetyltransferase. Exemplary genes conferring resistance to phenoxy proprionic acids and cyclohexones, such as sethoxydim and haloxyfop, are the Accl-S1, Accl-S2, and Accl-S3 genes.

(D) An herbicide that inhibits photosynthesis, such as a triazine (psbA and gs+genes) and a benzonitrile (nitrilase gene).

(E) Protoporphyrinogen oxidase (protox). Protox is necessary for the production of chlorophyll, which is necessary for all plant survival. The protox enzyme serves as the target for a variety of herbicidal compounds. These herbicides also inhibit growth of all the different species of plants present, causing their total destruction.

Genes that Confer or Improve Grain Quality (A) Genes that alter fatty acids. For example, fatty acids may be altered by: (1) down-regulation of stearyl-ACP desaturase to increase stearic acid content of the plant, by for example, transforming a plant with a nucleic acid encoding an anti-sense of stearyl-ACP desaturase; (2) elevating oleic acid via FAD-2 gene modification and/or decreasing linolenic acid via FAD-3 gene modification; (3) altering conjugated linolenic or linoleic acid content; and/or (4) altering LEC1, AGP, Dek1, Superall, mi1ps, and various Ipa genes such as Ipa1, Ipa3, hpt or hggt.

(B) Genes that alter phosphorus content. For example, phosphorus content may be altered by: (1) introduction of a phytase-encoding gene, which would enhance breakdown of phytate and add more free phosphate to the transformed plant; and/or (2) up-regulation of a gene that reduces phytate content.

(C) Genes that alter carbohydrates. This can be effected, for example, by altering a gene for an enzyme that affects the branching pattern of starch or a gene altering thioredoxin Bacillus subtilis levansucrase gene.

(D) Altered antioxidant content or composition, such as alteration of tocopherol or tocotrienols.

(E) Altered essential seed amino acids.

Genes that Control Male Sterility

There are several methods of conferring genetic male sterility available, such as multiple mutant genes at separate locations within the genome that confer male sterility. In addition to these methods, a system of nuclear male sterility may be used, which system includes: identifying a gene that is critical to male fertility; silencing this gene; removing the native promoter from the gene and replacing it with an inducible promoter; inserting this genetically engineered gene back into the plant; and creating a plant that is male sterile because the inducible promoter is not "on," resulting in the male fertility gene not being transcribed. Fertility may be restored by inducing, or turning "on," the promoter, which in turn allows the gene that confers male fertility to be transcribed.

(A) Introduction of a deacetylase gene under the control of a tapetum-specific promoter and with the application of the chemical Ni-Ac-PPT.

(B) Introduction of various stamen-specific promoters.

(C) Introduction of the barnase and the barstar genes.

Genes that Create a Site for Site Specific DNA Integration

This includes the introduction of FRT sites that may be used in the FLP/FRT system and/or Lox sites that may be used in the Cre/Loxp system. Other systems that may be used include the Gin recombinase of phage Mu, the Pin recombinase of E. coli, and the R/RS system of the pSRi plasmid.

Genes that Affect Abiotic Stress Resistance (A) Genes that affect abiotic stress resistance (including but not limited to flowering, seed development, enhancement of nitrogen utilization efficiency, altered nitrogen responsiveness, drought resistance or tolerance, cold resistance or tolerance, and salt resistance or tolerance) and increased yield under stress. For example, water use efficiency can be altered through alteration of malate. In addition, various genes, including CBF genes and transcription factors, can be effective in mitigating the negative effects of freezing, high salinity, and drought on plants, as well as conferring other positive effects on plant phenotype. Abscisic acid can be altered in plants, resulting in improved plant phenotype, such as increased yield and/or increased tolerance to abiotic stress. Cytokinin expression can be modified resulting in plants with increased stress tolerance, such as drought tolerance, and/or increased yield. Nitrogen utilization can be enhanced and/or nitrogen responsiveness can be altered. Ethylene can be altered. Plant transcription factors or transcriptional regulators of abiotic stress can also be altered.

(B) Improved tolerance to water stress from drought or high salt water condition.

(C) Improved water stress tolerance through increased mannitol levels via the bacterial mannitol-1-phosphate dehydrogenase gene.

Other genes and transcription factors that affect plant growth and agronomic traits such as yield, flowering, plant growth, lodging, and/or plant structure, can be introduced or introgressed into plants.

Genes that Confer Agronomic Enhancements, Nutritional Enhancements, or Industrial Enhancements Genes that alter enzyme activity for improved disease resistance and/or improved plant or grain quality may be introduced or introgressed into plants. For example, lipoxygenase levels can be altered to improve disease resistance and/or to improve the quality of the grain, resulting in improved flavor for beer, cereal, and other food products made from the grain. Another enzyme whose activity can be altered is beta-glucanase for improved plant and/or grain quality. Yet another enzyme whose activity can be altered is polyphenol oxidase for improved plant and/or grain quality.

Methods for Barley Transformation

Numerous methods for plant transformation have been developed, including biological and physical plant transformation protocols. In addition, expression vectors and in vitro culture methods for plant cell or tissue transformation and regeneration of plants are available.

Agrobacterium-Mediated Transformation. One method for introducing an expression vector into plants is based on the natural transformation system of Agrobacterium. A.tumefaciens and A. rhizogenes, which are plant pathogenic soil bacteria that genetically transform plant cells. The Ti and Ri plasmids of A. tumefaciens and A. rhizogenes, respectively, carry genes responsible for genetic transformation of the plant.

Direct Gene Transfer. Several methods of plant transformation, collectively referred to as direct gene transfer, have been developed as an alternative to Agrobacterium-mediated transformation. A generally applicable method of plant transformation is microprojectile-mediated transformation, wherein DNA is carried on the surface of microprojectiles measuring 1 to 4 pm. The expression vector is introduced into plant tissues with a biolistic device that accelerates the microprojectiles to speeds of 300 to 600 m/s, which is sufficient to penetrate plant cell walls and membranes.

Another method for physical delivery of DNA to plants is sonication of target cells. Alternatively, liposome and spheroplast fusion can be used to introduce expression vectors into plants. Direct uptake of DNA into protoplasts using $CaCl_2$ precipitation, polyvinyl alcohol or polyLornithine has also been reported. Electroporation of protoplasts and whole cells and tissues has also been described. Following transformation of barley target tissues, expression of the above-described selectable marker genes allows for preferential selection of transformed cells, tissues and/or plants, using regeneration and selection methods.

The foregoing methods for transformation could be used for producing a transgenic variety. The transgenic variety could then be crossed with another (non-transformed or transformed) variety in order to produce a new transgenic variety. Alternatively, a genetic trait that has been engineered into a particular barley cultivar using the foregoing transformation techniques could be moved into another cultivar using traditional backcrossing techniques that are known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple X by Y cross, or the process of backcrossing, depending on the context.

Genetic Marker Profile Through SSR and First Generation Progeny

In addition to phenotypic observations, a plant can also be identified by its genotype. The genotype of a plant can be characterized through a genetic marker profile, which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as microsatellites, and Single Nucleotide Polymorphisms (SNPs).

Particular markers used for these purposes are not limited to any particular set of markers, but are envisioned to include any type of marker and marker profile that provides a means of distinguishing varieties. One method of comparison is to use only homozygous loci for BG 104.

In addition to being used for identification of barley cultivar BG 104 and plant parts and plant cells of cultivar BG 104, the genetic profile may be used to identify a barley plant produced through the use of BG 104 or to verify a pedigree for progeny plants produced through the use of BG 104. The genetic marker profile can also be useful in breeding and developing backcross conversions.

Means of performing genetic marker profiles using SSR polymorphisms are known. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. PCR detection uses two oligonucleotide primers flanking the polymorphic segment of repetitive DNA. Repeated cycles of heat denaturation of the DNA, followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties, all SSR profiles may be performed in the same lab.

The SSR profile of barley plant BG 104 can be used to identify plants comprising BG 104 as a parent, since such plants will comprise the same homozygous alleles as BG 104. Because the barley variety is essentially homozygous at all relevant loci, most loci should have only one type of allele present. In contrast, a genetic marker profile of an $F_1$ progeny should be the sum of those parents, e.g., if one parent was homozygous for allele x at a particular locus, and the other parent homozygous for allele y at that locus, then the $F_1$ progeny will be xy (heterozygous) at that locus. Subsequent generations of progeny produced by selection and breeding are expected to be of genotype x (homozygous), y (homozygous), or xy (heterozygous) for that locus position. When the $F_1$ plant is selfed or sibbed for successive filial generations, the locus should be either x or y for that position.

In addition, plants and plant parts substantially benefiting from the use of BG 104 in their development, such as BG 104 comprising a backcross conversion, transgene, or genetic sterility factor, may be identified by having a molecular marker profile with a high percent identity to BG 104. In an embodiment, such a percent identity might be 95%, 96%, 97%, 98%, 99%, 99.5%, or 99.9% identical to BG 104.

The SSR profile of BG 104 also can be used to identify essentially derived varieties and other progeny varieties developed from the use of BG 104, as well as cells and other plant parts thereof. Progeny plants and plant parts produced using BG 104 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from BG 104, as measured by either percent identity or percent similarity. Such progeny may be further characterized as being within a pedigree distance of BG 104, such as within 1, 2, 3, 4, 5, or more cross pollinations to a barley plant other than BG 104 or a plant that has BG 104 as a progenitor. Unique molecular profiles may be identified with other molecular tools such as SNPs and RFLPs.

While determining the SSR genetic marker profile of a plant as described above, several unique SSR profiles may also be identified that did not appear in either parent plant. Such unique SSR profiles may arise during the breeding process from recombination or mutation. A combination of several unique alleles provides a means of identifying a plant variety, an $F_1$ progeny produced from such variety, and further progeny produced from such variety.

Gene Conversion

When the term "barley plant" is used in the context of the present innovation, this term also includes any gene conversions of that variety. Backcrossing methods can be used with the present innovation to improve or introduce a characteristic into the variety. For example, a variety may be backcrossed 1, 2, 3, 4, 5, 6, 7, 8, 9, or more times to the recurrent parent. The parental barley plant that contributes the gene for the desired characteristic is termed the "non-recurrent" or "donor" parent. This terminology refers to the fact that the nonrecurrent parent is used one time in the backcross protocol and therefore does not recur. The parental barley plant to which the gene or genes from the nonrecurrent parent are transferred is known as the recurrent parent, as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a barley plant is obtained wherein essentially all of the desired morphological and physiological characteristics of the recurrent parent are recovered in the converted plant, in addition to the single transferred gene from the nonrecurrent parent.

The selection of a suitable recurrent parent contributes to a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological, constitution of the original variety. The choice of the particular nonrecurrent parent will depend on the purpose of the backcross. One of the major purposes is to add commercially desirable, agronomically important traits to the plant. The exact backcrossing protocol will depend on the characteristic or trait being altered. Although backcrossing methods are simplified when the characteristic being transferred is a dominant allele, a recessive allele may also be transferred. In this instance, it may be necessary to introduce a test of the progeny to determine if the desired characteristic has been successfully transferred.

Many single gene traits have been identified that are not regularly selected for in the development of a new variety, but that can be improved by backcrossing techniques. Single gene traits may or may not be transgenic. Examples of these traits include, but are not limited to, male sterility, waxy starch, herbicide tolerance or resistance, resistance for bacterial, fungal, or viral disease, insect resistance or tolerance, male fertility, enhanced nutritional quality, industrial usage, yield stability, and yield enhancement. These genes are generally inherited through the nucleus.

Mutation Breeding

Mutation breeding is another method of introducing new traits into barley cultivar BG 104. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation, such as X-rays, Gamma rays (e.g. cobalt 60 or cesium 137), neutrons (product of nuclear fission by uranium 235 in an atomic reactor), Beta radiation (emitted from radioisotopes such as phosphorus 32 or carbon 14), or ultraviolet radiation (for example, from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Once a desired trait is observed through mutagenesis the trait may then be incorporated into existing germplasm by traditional breeding techniques. In addition, mutations created in other barley plants may be used to produce a backcross conversion of barley cultivar BG 104 that comprises such mutations. Further embodiments include the treatment of BG 104 with a mutagen and the plant produced by mutagenesis of BG 104.

TABLES

In one aspect of the present disclosure, barley cultivar BG 104 was tested for agronomic performance. Specifically, grain yield was examined for BG 104 in comparison to three other barley varieties, specifically, BG 161, BG 006, and BG 46e. The following Tables 2 through 4 show this comparison. In each table, column 1 lists the cultivars that were compared (i.e., BG 104, BG 161, BG 006, and BG 46e). Column 2 of Tables 2 and 3 shows the grain yield average across the 3 growing locations in terms of bushels per acre (Bu/a). Column 3 of Tables 2 and 3 shows the grain yield average across 2 irrigated locations (i.e., Bozeman, Montana and Idaho Falls, Idaho), again measured in bushels per acre. Column 4 shows the grain yield average in Bozeman, Montana only, while column 5 shows the grain yield average in Idaho Falls, Idaho, and column 6 shows the grain yield average in Belfield, N. Dak. Table 2 shows the information described above for testing conducted in 2010, while Table 3 shows testing results in 2011.

TABLE 2

| | Yield Average (3 locations) | Yield Average (Bozeman & Idaho Falls - irrigated) | Bozeman, MT | Idaho Falls, ID | Belfield, ND |
| --- | --- | --- | --- | --- | --- |
| BG 104 | 60.0 | 75.6 | 72.7 | 78.5 | 28.9 |
| BG 161 | 48.5 | 65.1 | 63.2 | 66.9 | 15.3 |
| BG 006 | 66.4 | 82.2 | 75.3 | 89.0 | 34.8 |
| BG 46e | 52.5 | 67.4 | 70.3 | 64.4 | 22.9 |

Grain Yield of BG 104 in three locations of adaptability, 2010

TABLE 3

| | Yield Average (3 locations) | Yield Average (Bozeman & Idaho Falls - irrigated) | Bozeman, MT | Idaho Falls, ID | Belfield, ND |
| --- | --- | --- | --- | --- | --- |
| BG 104 | 61 | 81 | 77 | 84 | 23 |
| BG 161 | N/A | 69 | 67 | 71 | N/A |
| BG 006 | 59 | 74 | 76 | 72 | 28 |

Grain Yield of BG 104 in three locations of adaptability, 2011

As can be seen from the results shown in Table 2, BG 104 exhibits an increased grain yield over BG 46e and BG 161, while exhibiting less grain yield than BG 006. However, Table 3, which includes testing from 2011, shows that BG 104 exhibited increased grain yield over BG 161 and BG 006.

Additional agronomical testing was performed on BG 104, as shown in Table 4 below. BG 104 was compared to barley varieties F5N09-0033, BG 161, BG 46e, and BG 006 to ascertain differences in maturity (i.e., heading date), plant height, and beta-glucan percentage. Column 1 in Table 4 lists the five barley varieties that were compared. Column 2 shows the heading date of each variety. Heading, as used herein, describes a specific date in which the spike exertion from the boot occurs, or exertion from the flag leaf of the barley plant. The heading measurements listed in Table 4 show the number of days between planting and when heading occurred. Column 3 lists the plant height, which is the average height in centimeters of the barley plants, as measured from the ground level to the tip of the head, excluding awns. Column 4 lists the beta-glucan percentage performed on a dry basis. The information provided in Table 4 is provided from plants and seeds measured in 2011 from plants grown in Idaho Falls, Id.

TABLE 4

| Variety | Heading | Plant Height | Beta-glucan % | |
|---|---|---|---|---|
| | | | Average | Range |
| BG 104 | 13 | 53 | 18.1 | 16.5-19.7 |
| F5N09-0033 | 13 | 53 | 17.8 | 15.7-19.5 |
| BG 161 | 15 | 48 | 15.5 | 15.0-16.0 |
| BG 46e | 15 | 79 | 15.2 | 13.7-16.7 |
| BG 006 | 11 | 55 | 8.4 | 8.1-8.6 |

Heading, Plant Height, and Beta-glucan Percentage, 2011

As can be seen in Table 4, heading of BG 104 occurs between heading of BG 46e and BG 006. Plant height of BG 104 is less than BG 46e and BG 006. Beta-glucan percentage is higher on average than BG 46e and BG 006. Thus, the BG 104 cultivar exhibits a much higher beta-glucan percentage than its BG 006 parent while having a slightly shorter plant height than its BG 46e parent. This results in a barley plant that is easier to harvest (i.e., its plant height allows for less lodging) and that exhibits a much higher beta-glucan percentage.

DEPOSIT INFORMATION

A deposit of the barley cultivar BG 104 disclosed above and recited in the appended claims has been made with the American Type Culture Collection (ATCC), 10801 University Boulevard, Manassas, Virginia 20110. The date of deposit was Jul. 26, 2017and the accession number for those deposited seeds of barley cultivar BG 104 is ATCC Accession No. PTA-124317. All restrictions on this deposit have been removed, and the deposit is intended to meet all of the requirements of 37 C.F.R. §§1.801-1.809. The deposit will be maintained in the depository for a period of thirty years, or five years after the last request, or for the enforceable life of the patent, whichever is longer, and will be replaced if necessary during that period.

All of the compositions and methods disclosed and claimed herein can be made and executed without undue experimentation in light of the present disclosure. While the compositions and methods of this disclosure have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the innovation as defined by the appended claims.

Although the application describes embodiments having specific structural features and/or methodological acts, it is to be understood that the claims are not necessarily limited to the specific features or acts described. Rather, the specific features and acts are merely illustrative of some embodiments that fall within the scope of the claims of the application.

What is claimed is:

1. A plant of barley cultivar BG 104, wherein a sample of seed of the barley cultivar BG 104 has been deposited under ATCC Accession No. PTA-124317.

2. A plant part of the plant of claim 1, wherein the plant part comprises at least one cell of the plant.

3. The plant part of claim 2, further defined as head, awn, leaf, pollen, ovule, embryo, cotyledon, hypocotyl, meristematic cell, root, root tip, pistil, anther, floret, seed, pericarp, spike, stem, and callus.

4. A seed from the plant of claim 1.

5. A tissue culture produced from the plant part of claim 3.

6. A barley plant regenerated from the tissue culture of claim 5.

7. A seed of barley cultivar BG 104, a representative sample of the seed of the barley cultivar BG 104 was deposited under ATCC Accession No. PTA-124317.

8. A barley plant, or a part thereof, produced by growing the seed of claim 7.

9. A method of producing a barley seed comprising crossing two barley plants and harvesting the resultant barley seed, wherein at least one barley plant is the barley plant of claim 8.

10. A barley seed produced by the method of claim 9, wherein the seed comprises all morphological and physiological characteristics of barley cultivar BG 104.

11. A barley plant, or a part thereof, produced by growing the seed of claim 10.

12. The method of claim 9, wherein the method further comprises crossing the plant of barley cultivar BG 104 with a second, distinct barley plant to produce an $F_1$ hybrid barley seed.

13. The method of claim 12, further comprising:
    (a) crossing a plant grown from the $F_1$ hybrid barley seed with itself or a different barley plant to produce a seed of a first progeny plant of a second generation;
    (b) growing a plant from the seed of the first progeny plant of the second generation and crossing the first progeny plant of the second generation with itself or a second plant to produce a seed of a second progeny plant of a third generation; and
    (c) repeating steps (a) and (b) using the second progeny plant of the third generation from step (b) in place of the plant grown from the $F_1$ hybrid barley seed in step (a), wherein steps (a) and (b) are repeated with sufficient inbreeding to produce an inbred barley plant derived from the barley cultivar BG 104 that comprises all morphological and physiological characteristics of barley cultivar BG 104.

14. A composition comprising the seed of claim 7 comprised in plant seed growth media.

15. The composition of claim 14, wherein the growth media is soil or a synthetic cultivation medium.

16. A method of producing a commodity plant product comprising collecting the commodity plant product from the plant of claim 1.

17. The method of claim 16, wherein the commodity plant product is grain, flour, bran, baked goods, cereals, pasta, beverages, malts, or medicines.

18. A barley commodity plant product produced by the method of claim 17, wherein the commodity plant product comprises at least one cell of barley cultivar BG 104.

19. A plant produced by introducing a single locus conversion into barley cultivar BG 104, or a selfed progeny thereof comprising the single locus conversion, wherein the single locus conversion is introduced into the barley cultivar BG 104 by backcrossing or genetic transformation and wherein a sample of seed of barley cultivar BG 104 has been deposited under ATCC Accession No. PTA-124317, wherein the plant comprises all morphological and physiological characteristics of barley cultivar BG 104.

20. The plant of claim 19, wherein the single locus conversion comprises a transgene.

21. A seed that produces the plant of claim 19.

22. The seed of claim 21, wherein the single locus conversion confers male sterility, herbicide tolerance, insect resistance, pest resistance, disease resistance, modified fatty acid metabolism, abiotic stress resistance, altered seed amino acid composition, site-specific genetic recombination, modified carbohydrate metabolism, or a combination thereof.

23. The seed of claim 22, wherein the single locus conversion confers tolerance to glyphosate, sulfonylurea, imidazolinone, dicamba, glufosinate, phenoxy proprionic acid, L-phosphinothricin, cyclohexone, cyclohexanedione, triazine, benzonitrile, or a combination thereof.

24. The seed of claim 21, wherein the single locus conversion comprises a transgene.

* * * * *